United States Patent [19]

Van der Knaap

[11] Patent Number: Plant 6,766

[45] Date of Patent: May 2, 1989

[54] CHRYSANTHEMUM PLANT NAMED APRICOT MONEYMAKER

[75] Inventor: Jacques C. M. Van der Knaap, De Lier, Netherlands

[73] Assignee: Fides Beheer B.V., De Lier, Netherlands

[21] Appl. No.: 128,495

[22] Filed: Dec. 1, 1987

[51] Int. Cl.[4] ..... A01H 5/00

[52] U.S. Cl. ..... Plt./74

[58] Field of Search ..... Plt./74

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Apricot Moneymaker, particularly characterized by its anemone capitulum type and flat capitulum form; apricot ray floret color, and by its apricot colored mature petaloids which form around the disc florets.

1 Drawing Sheet

The present invention comprises a new and distinct cultivar of Chrysanthemum, botanically known as *Chrysanthemum morifolium,* and referred to by the cultivar name Apricot Moneymaker.

Apricot Moneymaker is a spontaneous mutation of Moneymaker, disclosed in a pending application of applicant. Apricot Moneymaker was discovered by applicant in 1985 while growing in a cultivated bed of the parent cultivar Moneymaker. The new cultivar was immediately recognized due to its apricot ray floret color, as compared with the light pink ray floret color of Moneymaker.

The first act of asexual reproduction of Apricot Moneymaker was accomplished when vegetative cuttings were taken following discovery in a controlled environment in De Lier, The Netherlands by a technician working under formulations established and supervised by applicant. Horticultural examination of selected units has demonstrated that the combination of characteristics as herein disclosed for Apricot Moneymaker are firmly fixed and are retained through successive generations of asexual reproduction.

Apricot Moneymaker has not been observed under all possible environmental conditions. The phenotype may vary significantly with variations in environment such as temperature, light intensity, and day length. The following observations, measurements and comparisons describe plants grown in De Lier, The Netherlands under greenhouse conditions which approximate those generally used in commercial practice.

The following traits have been repeatedly observed and are determined to be basic characteristics of Apricot Moneymaker, which in combination distinguish this Chrysanthemum as a new and distinct cultivar:

1. Flat capitulum form.
2. Anemone capitulum type.
3. Apricot ray floret color.
4. Diameter across the face of the capitulum is 45–50 mm.
5. The petaloids formed around the disc florets are generally similar in color to the ray florets, with the disc center being a deeper yellow.

In comparison to the parent cultivar Moneymaker, the new cultivar distinguishes from its parent only in the characteristic of color. Other mutations of Moneymaker are Pink Moneymaker and Lilac Moneymaker, both of which are disclosed in pending applications of applicant. These other varieties also distinguish from their parent, and from Apricot Moneymaker, primarily by flower color.

The accompanying photographic drawing shows in front view typical inflorescence and foliage characteristics of Apricot Moneymaker, with colors being as true as possible with illustrations of this type.

In the following description, color references are made to the Royal Horticultural Society Colour Chart. The color values were determined between 11:00 a.m. and 12:00 noon in August under natural daylight at De Lier, The Netherlands.

Classification:

*Botanical.*—*Chrysanthemum morifolium,* Ramat., cv. Apricot Moneymaker.

*Commercial.*—Cut anemone spray.

INFLORESCENCE

A. Capitulum:
- *Form.*—Flat.
- *Type.*—Anemone.
- *Diameter across face.*—45–50 mm.

B. Corolla of ray florets:
- *Color (general tonality from a distance of three meters).*—Apricot.
- *Color (upper surface).*—8C (16D to 16A toward center in late October to early November).
- *Color (under surface).*—Somewhat lighter than 8C.

C. Corolla of disc florets:
- *Color.*—Green 145A-B (immature) maturing to a golden yellow; petaloids around disc florets closely match color of ray florets.

D. Reproductive organs:
- *Androecium.*—Present only in disc florets; numerous.
- *Gynoecium.*—Present in both disc and ray florets; numerous.

PLANT

A. General appearance:
- *Height.*—90 cm.

B. Foliage:
- *Color (upper surface).*—137A.
- *Color (under surface).*—137B.
- *Shape.*—Deeply serrated.

I claim:

1. A new and distinct cultivar of Chrysanthemum plant named Apricot Moneymaker, as described and illustrated, and parts thereof.

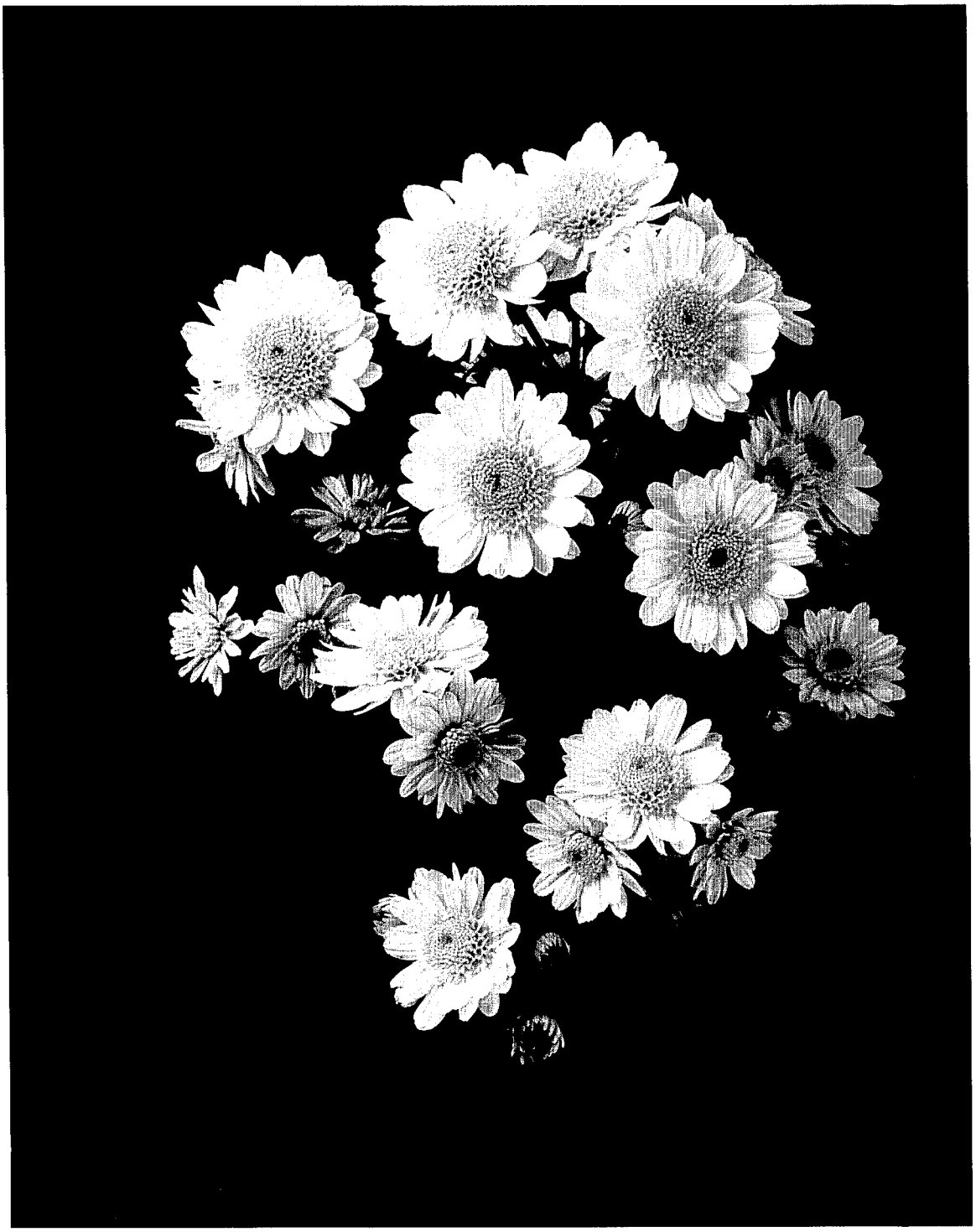

* * * * *